United States Patent [19]

Korenberg

[11] Patent Number: 5,945,305
[45] Date of Patent: Aug. 31, 1999

[54] NUCLEIC ACID ENCODING CONGENITAL HEART DISEASE PROTEIN AND PRODUCTS RELATED THERETO

[75] Inventor: Julie R. Korenberg, Los Angeles, Calif.

[73] Assignee: Cedars-Sinai Medical Center, Los Angeles, Calif.

[21] Appl. No.: 08/927,307

[22] Filed: Sep. 11, 1997

Related U.S. Application Data

[60] Provisional application No. 60/026,314, Sep. 19, 1996.

[51] Int. Cl.$^6$ .......................... C12N 15/00; C12N 15/63; C12N 15/85; C07H 21/04
[52] U.S. Cl. ................... 435/69.1; 435/320.1; 435/325; 435/354; 435/366; 435/440; 536/23.1; 536/23.5; 536/24.3; 536/24.31
[58] Field of Search ................................... 435/69.1, 440, 435/320.1, 325, 354, 366; 536/23.1, 23.5, 24.3, 24.31

[56] References Cited

U.S. PATENT DOCUMENTS 5,346,815  9/1994  Krulwich et al. ..................... 435/69.1

OTHER PUBLICATIONS

Doolittle, Of URFS and ORFS, A Primer on How to Analyze Derived Amino Acid Sequences, University Science Books, Mill Valley CA (1986), p. 7.
Wadey et al., Isolation of a Gene Encoding an Integral Membrane Protein from the Vicinity of a Balanced Translocation Breakpoint Associated with DiGeorge Syndrome, Human Molecular Genetics 4 (6), 1027–1033 (1995).
Turbay et al., Molecular Cloning, Chromosomal Mapping, and Characterization of the Human Cardiac–Specific Homeobox Gene hCsx, Molecular Medicine 2 (1) (Jan. 1996).
Hillier et al., WashU–Merck EST Project, ID No.: H98008 (Dec. 12, 1995).
Marra et al., WashU–HHMI Mouse EST Project, ID No.: W41440 (Sep. 11, 1996).
Marra et al., WashU–HHMI Mouse EST Project, ID No.: W53931 (Jun. 03, 1996).
Reeck et al., "Homology" in Proteins and Nucleic Acids: A Terminolgy Muddle and a Way Out of It, Cell 50, 667 (Aug. 28, 1987).
Hillier et al., "Homo sapiens cDNA clone 251486 3'", The WashU–Merck EST Project, ID # HS008249, (1995).
Hubert et al., Down Syndrome congenital heart disease: Physical and transcriptional mapping of the candidate region using BACs and PACs, Am. J. Hum. Gen., 57(4):A13 (1995).
Julie R. Korenberg, "Toward A Molecular Understanding Of Down Syndrome", The Phenotypic Mapping of Down Syndrome and Other Aneuploid Conditions, 87–115 (1993).
Marra et al., "Mus Musculus cDNA clone 3511675'", The WashU–HHMI Mouse EST Project, ID # MM44015 (1996).

Antonarakis et al., "Molecular Mapping of Chromosome 21 and the region responsible for Down Syndrome", Molecular and Cytogenetic Studies of Non–Disjunction, 29–43 (1989).
Chumakov et al., "Continuum of overlapping clones spanning the entire human chromosome 21q" Nature 359:380–87 (1992).
Cohen et al., "A first–generation physical map of the human genome", Nature 366:698–701 (1993).
Ioannou et al., "A new bacteriophage P1–derived vector for the propagation of large human DNA fragments", Nature Genetics 6:84–89 (1994).
Korenberg et al., "Down Syndrome: Molecular Mapping of the Congenital Heart Disease and Duodenal Stenosis", Am. J. Hum. Genet. 50:294–302 (1992).
Korenberg et al., "Down syndrome phenotypes: The consequences of chromosomal imbalance", Proc. Natl. Acad. Sci. USA 91:4997–5001 (1994).
Korenberg et al., "A High Fidelity Physical Map of Human Chromosome 21q in Yeast Artificial Chromosomes", Genome Research 5:427–443 (1995).
Korenberg and Chen, Human cDNA mapping using a high–resolution R–banding technique and fluorescence in situ hybridization, Cytogenet Cell Genet. 69:196–200 (1995).
Morgan et al., "The selective isolation of novel cDNAs encoded by the regions surrounding the human interleukin 4 and 5 genes", Nucleic Acids Research 20(19):5173–5179 (1992).
Osoegawa et al., "An Integrated Map with Cosmid/PAC Contigs of a Mb Down Syndrome Critical Region", Genomics 32:375–387 (1996).
Patil, N., "A high resolution physical map of 2.5 Mbp of the Down syndrome region on chromosome 21", Human Molecular Genetics 3(10):1811–1817 (1994).
Shimizu et al., "Report of the Fifth International Workshop on Human Chromosome 21 Mapping 1994", Cytogenet Cell Genet., 70:147–182 (1995).
Shizuya et al., "Cloning and stable maintenance of 300–kiobase –pair fragments of human DNA in Escherichia coli using an F–factor–based vector", Proc. Natl. Acad. Sci. USA 89:8794–8797 (1992).
Wimmer et al., "A Drosophilia homologue of human Sp1 is a head–specific segmentation gene", Nature 366:690–694 (1993).

Primary Examiner—John L. LeGuyader
Assistant Examiner—Mark L. Shibuya
Attorney, Agent, or Firm—Pennie & Edmonds LLP

[57] ABSTRACT

In accordance with the present invention, there are provided novel Congenital Heart Disease (CHD) proteins. Nucleic acid sequences encoding such proteins and assays employing same are also disclosed. The invention CHD proteins can be employed in a variety of ways, for example, for the production of anti-CHD antibodies thereto, in therapeutic compositions and methods employing such proteins and/or antibodies.

24 Claims, 1 Drawing Sheet

FIG. 1

NUCLEIC ACID ENCODING CONGENITAL HEART DISEASE PROTEIN AND PRODUCTS RELATED THERETO

The present invention claims the benefit of U.S. Provisional Application Ser. No. 60/026,314, filed Sep. 19, 1996.

ACKNOWLEDGMENT

This invention was made with Government support under Grant Numbers HL50025 and HD17449, awarded by the National Institutes of Health. The Government has certain rights in this invention.

FIELD OF THE INVENTION

The present invention relates to nucleic acids and receptor proteins encoded thereby. Invention nucleic acids encode novel congenital heart disease related proteins. The invention also relates to methods for making and using such nucleic acids and proteins.

BACKGROUND OF THE INVENTION

Down syndrome (DS) usually caused by chromosome 21 trisomy and is a major cause of mental retardation and congenital heart (CHD) and gut disease affecting over 200,000 persons in the United States alone. The characteristic heart abnormalities in DS-CHD include atrioventricular canal and ventricular septal defects. Other features of DS include a set of characteristic facies, thymic abnormalities, increased risk of leukemia and early onset of Alzheimer-like dementia. Molecular analysis of rare patients with DS and partial chromosome 21 duplications and monosomies has led to the association of certain chromosomal regions with specific DS phenotypes (Korenberg et al., *Proc. Natl. Acad. Sci. USA* M91:4997–5001 (1994); Delebar et al., *Eur. J. Human. Genet.* 1:114–124 (1993); Antonarakis et al., *Progress in Clinical and Biological Research* 311:29–43 (1989)). Chromosome 21 is therefore a model for the study of human chromosomal aneuploidy and the construction of its physical map is of special interest.

Human chromosome 21 has a nearly complete physical map with a well characterized contiguous set of overlapping YACs spanning most of its length (Chumakov et al., *Nature* 359:380–387 (1992); Shimizu et al., *Cytogenet. Cell Genet.* 70:147–182 (1995); Korenberg et al., Genome Research 5:427–443 (1995)). The demand for sequence ready contigs and clones for gene isolation efforts has prompted the construction of numerous higher resolution contigs in cosmids (Patil et al., *Hum. Molec. Genet.* 3:1811–1817 (1995)) and more recently in PACs (Osoegawa et al., *Genomics* 32:375–387 (1996)). Considerable mapping efforts exist in the region from CBR to D21S55 due to the duplication of this region in partially trisomic individuals with several phenotypic features of DS including mental retardation. However, the distal and adjacent, 4–5 Mb D21S55 to MX1 region is also of interest due to its association with Down syndrome congenital heart disease (DS-CHD) as well as other characteristic features of DS (Korenberg et al., *Am. J. Hum. Genet.* 50:294–302 (1992), Korenberg et al. (1994)). Although non-chimeric YACs span this interval, three are not as yet any higher resolution physical maps are available for the entire D21S55 to MX1 region. Thus, higher resolution physical maps for the entire D21S55 to MX1 region are desired. In addition, there is a need in the art for an isolated nucleic acid, and isolated protein encoded thereby, associated with congenital heart disease (CHD).

BRIEF DESCRIPTION OF THE INVENTION

In accordance with the present invention, there are provided isolated nucleic acids encoding mammalian CHD (congenital heart disease) proteins. Further provided are vectors containing invention nucleic acids, probes that hybridize thereto, host cells transformed therewith, antisense oligonucleotides thereto and related compositions. The nucleic acid molecules described herein can be incorporated into a variety of expression systems known to those of skill in the art. In addition, the nucleic acid molecules of the present invention are useful as probes for assaying for the presence and/or amount of a CHD gene or mRNA transcript in a given sample. The nucleic acid molecules described herein, and oligonucleotide fragments thereof, are also useful as primers and/or templates in a PCR reaction for amplifying genes encoding CHD proteins.

In accordance with the present invention, there are also provided isolated mammalian CHD proteins. In addition, these proteins, or fragments thereof, are useful in bioassays, as immunogens for producing anti-CHD antibodies, or in therapeutic compositions containing such proteins and/or antibodies. Also provided are transgenic non-human mammals that express the invention protein.

Antibodies that are immunoreactive with invention CHD proteins are also provided. These antibodies are useful in diagnostic assays to determine levels of CHD proteins present in a given sample, e.g., tissue samples, Western blots, and the like. The antibodies can also be used to purify CHD proteins from crude cell extracts and the like. Moreover, these antibodies are considered therapeutically useful to counteract or supplement the biological effect of CHDs in vivo.

Methods and diagnostic systems for determining the levels of CHD protein in various tissue samples are also provided. These diagnostic methods can be used for monitoring the level of therapeutically administered CHD protein or fragments thereof to facilitate the maintenance of therapeutically effective amounts. These diagnostic methods can also be used to diagnose physiological disorders that result from abnormal levels of CHD protein.

DETAILED DESCRIPTION OF THE INVENTION

Figure 1:
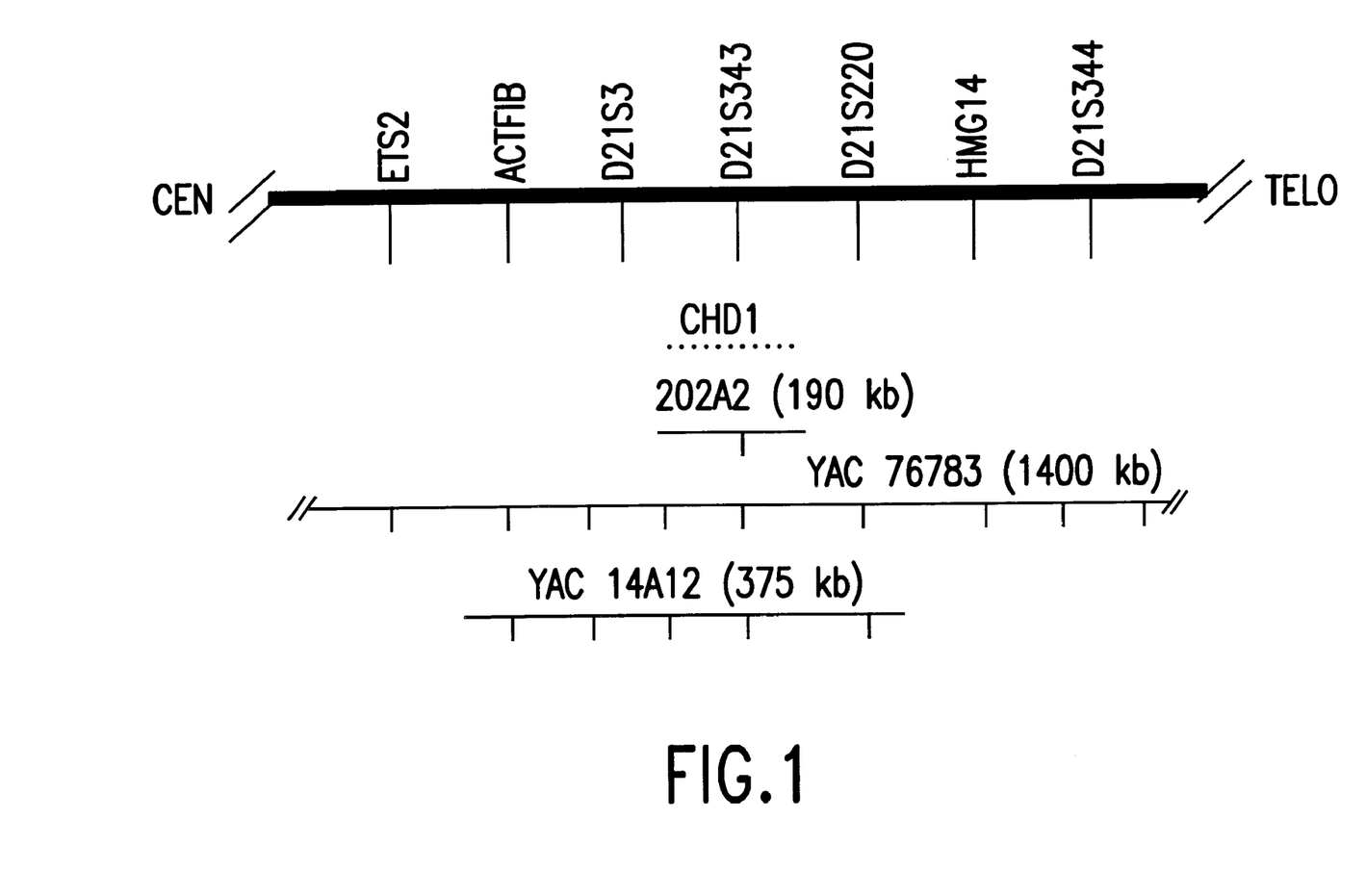
FIG. 1 shows a physical map of the localization of the CHD gene to a 190 kb region between D21S3 and D21S220 on chromosome 21. YACs 767B3 and 14A12 are shown for reference.

In accordance with the present invention, there are provided isolated nucleic acids, which encode a novel mammalian CHD (congenital heart disease) protein, and fragments thereof, wherein such nucleic acids can be obtained from human chromosome 21, specifically at the q22.2–22.3 locus, which is the site of chromosomal duplications that cause Down Syndrome Congenital Heart Disease (DS-CHD). As used herein, CHD proteins are those that encode a polypeptide specifically recognized by an antibody that also specifically recognizes a mammalian CHD protein (preferably human) including the sequence set forth in SEQ ID NO:2.

The nucleic acid molecules described herein are useful for producing invention proteins, when such nucleic acids are incorporated into a variety of protein expression systems known to those of skill in the art. In addition, such nucleic acid molecules or fragments thereof can be labeled with a readily detectable substituent and used as hybridization probes for assaying for the presence and/or amount of a CHD gene or MRNA transcript in a given sample. The nucleic acid molecules described herein, and fragments thereof, are also useful as primers and/or templates in a PCR reaction for amplifying genes encoding the invention protein described herein.

The term "nucleic acid" (also referred to as polynucleotides) encompasses ribonucleic acid (RNA) or deoxyribonucleic acid (DNA), probes, oligonucleotides, and primers. DNA can be either complementary DNA (CDNA) or genomic DNA, e.g. a gene encoding a CHD protein. One means of isolating a nucleic acid encoding an CHD polypeptide is to probe a mammalian genomic library with a natural or artificially designed DNA probe using methods well known in the art. DNA probes derived from the CHD gene are particularly useful for this purpose. DNA and CDNA molecules that encode CHD polypeptides can be used to obtain complementary genomic DNA, cDNA or RNA from mammalian (e.g., human, mouse, rat, rabbit, pig, and the like), or other animal sources, or to isolate related cDNA or genomic clones by the screening of cDNA or genomic libraries, by methods described in more detail below. Examples of nucleic acids are RNA, cDNA, or isolated genomic DNA encoding an CHD polypeptide. Such nucleic acids may include, but are not limited to, nucleic acids having substantially the same nucleotide sequence as set forth in SEQ ID NO:1, SEQ ID NO:7, SEQ ID NO:8, or at least nucleotides 39–902 of SEQ ID NO:1.

Use of the terms "isolated" and/or "purified" in the present specification and claims as a modifier of DNA, RNA, polypeptides or proteins means that the DNA, RNA, polypeptides or proteins so designated have been produced in such form by the hand of man, and thus are separated from their native in vivo cellular environment. As a result of this human intervention, the recombinant DNAs, RNAs, polypeptides and proteins of the invention are useful in ways described herein that the DNAs, RNAs, polypeptides or proteins as they naturally occur are not.

As used herein, "mammalian" refers to the variety of species from which the invention CHD protein is derived, e.g., human, rat, mouse, rabbit, monkey, baboon, chicken, bovine, porcine, ovine, canine, feline, and the like. A preferred CHD protein herein, is human CHD.

In one embodiment of the present invention, cDNAs encoding the invention CHD proteins disclosed herein include substantially the same nucleotide sequence as set forth in SEQ ID NO:1, SEQ ID NO:7 or SEQ ID NO:8. Preferred cDNA molecules encoding the invention proteins include the same nucleotide sequence as nucleotides 39–902 of SEQ ID NO:1.

As employed herein, the term "substantially the same nucleotide sequence" refers to DNA having sufficient identity to the reference polynucleotide, such that it will hybridize to the reference nucleotide under moderately stringent hybridization conditions. In one embodiment, DNA having substantially the same nucleotide sequence as the reference nucleotide sequence encodes substantially the same amino acid sequence as that set forth in SEQ ID NO:2, or a larger amino acid sequence including SEQ ID NO:2, or the CHD encoding portions of SEQ ID NO:7 or SEQ ID NO:8. In another embodiment, DNA having "substantially the same nucleotide sequence" as the reference nucleotide sequence has at least 60% identity with respect to the reference nucleotide sequence. DNA having at least 70%, more preferably at least 90%, yet more preferably at least 95%, identity to the reference nucleotide sequence is preferred.

This invention also encompasses nucleic acids which differ from the nucleic acids shown in SEQ ID NO:1, SEQ ID NO:7 and SEQ ID NO:8, but which have the same phenotype. Phenotypically similar nucleic acids are also referred to as "functionally equivalent nucleic acids". As used herein, the phrase "functionally equivalent nucleic acids" encompasses nucleic acids characterized by slight and non-consequential sequence variations that will function in substantially the same manner to produce the same protein product(s) as the nucleic acids disclosed herein. In particular, functionally equivalent nucleic acids encode polypeptides that are the same as those disclosed herein or that have conservative amino acid variations, or that encode larger polypeptides that include SEQ ID NO:2, or the CHD encoding portions of SEQ ID NO:7 or SEQ ID NO:8. For example, conservative variations include substitution of a non-polar residue with another non-polar residue, or substitution of a charged residue with a similarly charged residue. These variations include those recognized by skilled artisans as those that do not substantially alter the tertiary structure of the protein.

Further provided are nucleic acids encoding CHD polypeptides that, by virtue of the degeneracy of the genetic code, do not necessarily hybridize to the invention nucleic acids under specified hybridization conditions. Preferred nucleic acids encoding the invention polypeptide are comprised of nucleotides that encode substantially the same amino acid sequence set forth in SEQ ID NO:2, or the CHD encoding portions of SEQ ID NO:7 or SEQ ID NO:8.

Thus, an exemplary nucleic acid encoding an invention CHD protein may be selected from:

(a) DNA encoding the amino acid sequence set forth in SEQ ID NO:2, or the CHD encoding portions of SEQ ID NO:7 or SEQ ID NO:8

(b) DNA that hybridizes to the DNA of (a) under moderately stringent conditions, wherein said DNA encodes biologically active CHD, or (c) DNA degenerate with respect to either (a) or (b) above, wherein said DNA encodes biologically active CHD.

Hybridization refers to the binding of complementary strands of nucleic acid (i.e., sense:antisense strands or probe:target-DNA) to each other through hydrogen bonds, similar to the bonds that naturally occur in chromosomal DNA. Stringency levels used to hybridize a given probe with target-DNA can be readily varied by those of skill in the art.

The phrase "stringent hybridization" is used herein to refer to conditions under which polynucleic acid hybrids are stable. As known to those of skill in the art, the stability of hybrids is reflected in the melting temperature ($T_m$) of the hybrids. In general, the stability of a hybrid is a function of sodium ion concentration and temperature. Typically, the hybridization reaction is performed under conditions of lower stringency, followed by washes of varying, but higher, stringency. Reference to hybridization stringency relates to such washing conditions.

As used herein, the phrase "moderately stringent hybridization" refers to conditions that permit target-DNA to bind a complementary nucleic acid that has about 60% identity, preferably about 75% identity, more preferably about 85% identity to the target DNA; with greater than about 90% identity to target-DNA being especially preferred. Preferably, moderately stringent conditions are conditions equivalent to hybridization in 50% formamide, 5× Denhart's solution, 5× SSPE, 0.2% SDS at 42° C., followed by washing in 0.2× SSPE, 0.2% SDS, at 65° C.

The phrase "high stringency hybridization" refers to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High stringency conditions can be provided, for example, by hybridization in 50% formamide, 5× Denhart's solution, 5× SSPE, 0.2% SDS at 42° C., followed by washing in 0.1× SSPE, and 0.1% SDS at 65° C.

The phrase "low stringency hybridization" refers to conditions equivalent to hybridization in 10% formamide, 5× Denhart's solution, 6× SSPE, 0.2% SDS at 42° C., followed by washing in 1× SSPE, 0.2% SDS, at 50° C. Denhart's solution and SSPE (see, e.g., Sambrook et al., *Molecular Cloning, A Laboratory Manual*, Cold Spring Harbor Laboratory Press, 1989) are well known to those of skill in the art as are other suitable hybridization buffers.

As used herein, the term "degenerate" refers to codons that differ in at least one nucleotide from a reference nucleic acid, e.g., SEQ ID NO:1, SEQ ID NO:7 or SEQ ID NO:8, but encode the same amino acids as the reference nucleic acid. For example, codons specified by the triplets "UCU", "UCC", "UCA", and "UCG" are degenerate with respect to each other since all four of these codons encode the amino acid serine.

Preferred nucleic acids encoding the invention polypeptide(s) hybridize under moderately stringent, preferably high stringency, conditions to substantially the entire sequence, or substantial portions (i.e., typically at least 15–30 nucleotides) of the nucleic acid sequence set forth in SEQ ID NO:1, SEQ ID NO:7 or SEQ ID NO:8.

The invention nucleic acids can be produced by a variety of methods well-known in the art, e.g., the methods described herein, employing PCR amplification using oligonucleotide primers from various regions of SEQ ID NO:1, SEQ ID NO:7 or SEQ ID NO:8, and the like.

In accordance with a further embodiment of the present invention, optionally labeled CHD-encoding cDNAs, or fragments thereof, can be employed to probe library(ies) (e.g., cDNA, genomic, and the like) for additional nucleic acid sequences encoding novel mammalian CHD proteins. As described in Example 3, construction of mammalian cDNA libraries, preferably a human trisomy 21 fetal brain cDNA library, is well-known in the art. Screening of such a cDNA library is initially carried out under low-stringency conditions, which comprise a temperature of less than about 42° C., a formamide concentration of less than about 50%, and a moderate to low salt concentration.

Presently preferred probe-based screening conditions comprise a temperature of about 37° C., a formamide concentration of about 20%, and a salt concentration of about 5× standard saline citrate (SSC; 20× SSC contains 3M sodium chloride, 0.3M sodium citrate, pH 7.0). Such conditions will allow the identification of sequences which have a substantial degree of similarity with the probe sequence, without requiring perfect homology. The phrase "substantial similarity" refers to sequences which share at least 50% homology. Preferably, hybridization conditions will be selected which allow the identification of sequences having at least 70% homology with the probe, while discriminating against sequences which have a lower degree of homology with the probe. As a result, nucleic acids having substantially the same nucleotide sequence as nucleotides 39–902 of SEQ ID NO:1 are obtained.

As used herein, a nucleic acid "probe" is single-stranded DNA or RNA, or analogs thereof, that has a sequence of nucleotides that includes at least 14, preferably at least 20, more preferably at least 50, contiguous bases that are the same as (or the complement of) any 14 or more contiguous bases set forth in any of SEQ ID NO:1, SEQ ID NO:7 or SEQ ID NO:8. Preferred regions from which to construct probes include 5' and/or 3' coding regions of SEQ ID NO:1, SEQ ID NO:7 or SEQ ID NO:8. In addition, the entire cDNA encoding region of an invention CHD protein, or the entire sequence corresponding to SEQ ID NO:1, SEQ ID NO:7 or SEQ ID NO:8, may be used as a probe. Probes may be labeled by methods well-known in the art, as described hereinafter, and used in various diagnostic kits.

As used herein, the terms "label" and "indicating means" in their various grammatical forms refer to single atoms and molecules that are either directly or indirectly involved in the production of a detectable signal. Any label or indicating means can be linked to invention nucleic acid probes, expressed proteins, polypeptide fragments, or antibody molecules. These atoms or molecules can be used alone or in conjunction with additional reagents. Such labels are themselves well-known in clinical diagnostic chemistry.

The labeling means can be a fluorescent labeling agent that chemically binds to antibodies or antigens without denaturation to form a fluorochrome (dye) that is a useful immunofluorescent tracer. A description of immunofluorescent analytic techniques is found in DeLuca, "Immunofluorescence Analysis", in *Antibody As a Tool*, Marchalonis et al., eds., John Wiley & Sons, Ltd., pp. 189–231 (1982), which is incorporated herein by reference.

In one embodiment, the indicating group is an enzyme, such as horseradish peroxidase (HRP), glucose oxidase, and the like. In another embodiment, radioactive elements are employed labeling agents. The linking of a label to a substrate, i.e., labeling of nucleic acid probes, antibodies, polypeptides, and proteins, is well known in the art. For instance, an invention antibody can be labeled by metabolic incorporation of radiolabeled amino acids provided in the culture medium. See, for example, Galfre et al., *Meth. Enzymol.*, 73:3–46 (1981). Conventional means of protein conjugation or coupling by activated functional groups are particularly applicable. See, for example, Aurameas et al., *Scand. J. Immunol.*, Vol. 8, Suppl. 7:7–23 (1978), Rodwell et al., *Biotech.*, 3:889–894 (1984), and U.S. Pat. No. 4,493, 795.

In accordance with another embodiment of the present invention, there are provided isolated mammalian CHD proteins (preferably human), polypeptides, and fragments thereof encoded by invention nucleic acid. The phrase "CHD" refers to substantially pure native CHD protein, or recombinantly produced proteins, including naturally occurring allelic variants thereof encoded by mRNA generated by alternative splicing of a primary transcript, and further including fragments thereof which retain at least one native biological activity, such as immunogenicity. Preferably, CHD proteins referred to herein, are those polypeptides specifically recognized by an antibody that also specifically recognizes a CHD protein (preferably human) including the sequence set forth in SEQ ID NO:2, or the CHD encoding portions of SEQ ID NO:7 or SEQ ID NO:8. Invention isolated CHD proteins are free of cellular components and/or contaminants normally associated with a native in vivo environment.

The invention proteins are further characterized by being primarily expressed in adult heart and skeletal muscle with lower level ubiquitous expression (described in Example 4). Differentially higher levels of CHD expression are observed in adult heart cells relative to skeletal muscle cells. The major transcript in the heart tissue is 2.4 kb in size while the major transcript in muscle is at 1.2 kb (observed by a Northern blot assay). Heart tissue also has a minor transcript around 1.2 kb and skeletal muscle has a minor transcript at 2.6 kb. Thus, splice variant cDNA transcripts encoding a CHD family of proteins are clearly contemplated by the present invention. As used herein, the phrase "differentially expressed" means that naturally occurring RNA encoding the invention proteins can be detected in substantially higher levels in adult heart tissue relative to skeletal muscle tissue.

CHD is contemplated as the gene, which when defective or present as a duplication, is responsible for Down Syndrome Congenital Heart Disease. Additional roles for CHD were further evaluated by database homology searches using BLAST X/N and TIGR database analyses. Results of these searches indicate that CHD shows moderate homology to a myeloid differentiation primary response gene and lower level homologies to transcription factors suggesting a possible role in embryonic differentiation. In addition, CHD shares some homologies with rat polymeric immunoglobulin receptor, a myosin heavy chain smooth muscle isoform, and aminolevulinic acid synthase.

As described herein, the location of CHD relative to the known DS-CHD region on chromosome 21, the expression pattern in heart and skeletal muscle, the presence of the transcript at day 53 and 55 in development, and the sequence homologies implicate CHD protein in heart development and as a cause of congenital heart disease.

Presently preferred CHD proteins of the invention include amino acid sequences that are substantially the same as the protein sequence set forth in SEQ ID NO:2, or the CHD encoding portions of SEQ ID NO:7 or SEQ ID NO:8, as well as biologically active, modified forms thereof. Those of skill in the art will recognize that numerous residues of the above-described sequences can be substituted with other, chemically, sterically and/or electronically similar residues without substantially altering the biological activity of the resulting receptor species. In addition, larger polypeptide sequences containing substantially the same sequence as SEQ ID NQ:2, or the CHD encoding portions of SEQ ID NO:7 or SEQ ID NO:8, therein (e.g., splice variants and fusion proteins) are contemplated.

As employed herein, the term "substantially the same amino acid sequence" refers to amino acid sequences having at least about 70% identity with respect to the reference amino acid sequence, and retaining comparable functional and biological activity characteristic of the protein defined by the reference amino acid sequence. Preferably, proteins having "substantially the same amino acid sequence" will have at least about 80%, more preferably 90% amino acid identity with respect to the reference amino acid sequence; with greater than about 95% amino acid sequence identity being especially preferred. It is recognized, however, that polypeptides (or nucleic acids referred to hereinbefore) containing less than the described levels of sequence identity arising as splice variants or that are modified by conservative amino acid substitutions, or by substitution of degenerate codons are also encompassed within the scope of the present invention.

The term "biologically active" or "functional", when used herein as a modifier of invention CHD protein(s), or polypeptide fragment thereof, refers to a polypeptide that exhibits functional characteristics similar to CHD. For example, one biological activity of CHD is the ability to act as an immunogen for the production of polyclonal and monoclonal antibodies that bind specifically to CHD. Thus, an invention nucleic acid encoding CHD will encode a polypeptide specifically recognized by an antibody that also specifically recognizes the CHD protein (preferably human) including the sequence set forth in SEQ ID NO:2, or the CHD encoding portions of SEQ ID NO:7 or SEQ ID NO:8. Such activity may be assayed by any method known to those of skill in the art. For example, a test-polypeptide encoded by a CHD cDNA can be used to produce antibodies, which are then assayed for their ability to bind to the protein including the sequence set forth in SEQ ID NO:2, or the CHD encoding portions of SEQ ID NO:7 or SEQ ID NO:8. If the antibody binds to the test-polypeptide and the protein including the sequence set forth in SEQ ID NO:2, or the CHD encoding portions of SEQ ID NO:7 or SEQ ID NO:8, with substantially the same affinity, then the polypeptide possesses the requisite biological activity.

The invention CHD proteins can be isolated by a variety of methods well-known in the art, e.g., the methods described in Example 3, the recombinant expression systems described herein, precipitation, gel filtration, ion-exchange, reverse-phase and affinity chromatography, and the like. Other well-known methods are described in Deutscher et al., *Guide to Protein Purification: Methods in Enzymology* Vol. 182, (Academic Press, (1990)), which is incorporated herein by reference. Alternatively, the isolated polypeptides of the present invention can be obtained using well-known recombinant methods as described, for example, in Sambrook et al., supra., 1989).

An example of the means for preparing the invention polypeptide(s) is to express nucleic acids encoding the CHD in a suitable host cell, such as a bacterial cell, a yeast cell, an amphibian cell (i.e., oocyte), or a mammalian cell, using methods well known in the art, and recovering the expressed polypeptide, again using well-known methods. Invention polypeptides can be isolated directly from cells that have been transformed with expression vectors as described below herein. The invention polypeptide, biologically active fragments, and functional equivalents thereof can also be produced by chemical synthesis. For example, synthetic polypeptides can be produced using Applied Biosystems, Inc. Model 430A or 431A automatic peptide synthesizer (Foster City, Calif.) employing the chemistry provided by the manufacturer.

The present invention also provides compositions containing an acceptable carrier and any of an isolated, purified CHD polypeptide, an active fragment thereof, or a purified, mature protein and active fragments thereof, alone or in combination with each other. These polypeptides or proteins can be recombinantly derived, chemically synthesized or purified from native sources. As used herein, the term "acceptable carrier" encompasses any of the standard pharmaceutical carriers, such as phosphate buffered saline solution, water and emulsions such as an oil/water or water/oil emulsion, and various types of wetting agents.

Also provided are antisense oligonucleotides having a sequence capable of binding specifically with any portion of an mRNA that encodes CHD polypeptides so as to prevent translation of the mRNA. The antisense oligonucleotide may have a sequence capable of binding specifically with any portion of the sequence of the cDNA encoding CHD polypeptides. As used herein, the phrase "binding specifically" encompasses the ability of a nucleic acid sequence to recognize a complementary nucleic acid sequence and to form double-helical segments therewith via the formation of hydrogen bonds between the complementary base pairs. An example of an antisense oligonucleotide is an antisense oligonucleotide comprising chemical analogs of nucleotides.

Compositions comprising an amount of the antisense oligonucleotide, described above, effective to reduce expression of CHD polypeptides by passing through a cell membrane and binding specifically with mRNA encoding CHD polypeptides so as to prevent translation and an acceptable hydrophobic carrier capable of passing through a cell membrane are also provided herein. Suitable hydrophobic carriers are described, for example, in U.S. Pat. Nos. 5,334,761; 4,889,953; 4,897,355, and the like. The acceptable hydrophobic carrier capable of passing through cell membranes may also comprise a structure which binds to a receptor specific for a selected cell type and is thereby taken up by cells of the selected cell type. The structure may be part of a protein known to bind to a cell-type specific receptor.

Antisense oligonucleotide compositions are useful to inhibit translation of mRNA encoding invention polypeptides. Synthetic oligonucleotides, or other antisense chemical structures are designed to bind to mRNA encoding CHD polypeptides and inhibit translation of mRNA and are useful as compositions to inhibit expression of CHD associated genes in a tissue sample or in a subject.

In accordance with another embodiment of the invention, kits for detecting mutations, duplications, deletions, rearrangements and aneuploidies in chromosome 21 at locus q22.2–22.3 comprising at least one invention probe or antisense nucleotide.

The present invention provides means to modulate levels of expression of CHD polypeptides by employing synthetic antisense oligonucleotide compositions (hereinafter SAOC) which inhibit translation of mRNA encoding these polypeptides. Synthetic oligonucleotides, or other antisense chemical structures designed to recognize and selectively bind to mRNA, are constructed to be complementary to portions of the CHD coding strand or nucleotide sequences shown in SEQ ID NO:1, SEQ ID NO:7 or SEQ ID NO:8. The SAOC is designed to be stable in the blood stream for administration to a subject by injection, or in laboratory cell culture conditions. The SAOC is designed to be capable of passing through the cell membrane in order to enter the cytoplasm of the cell by virtue of physical and chemical properties of the SAOC which render it capable of passing through cell membranes, for example, by designing small, hydrophobic SAOC chemical structures, or by virtue of specific transport systems in the cell which recognize and transport the SAOC into the cell. In addition, the SAOC can be designed for administration only to certain selected cell populations by targeting the SAOC to be recognized by specific cellular uptake mechanisms which bind and take up the SAOC only within select cell populations.

For example, the SAOC may be designed to bind to a receptor found only in a certain cell type, as discussed supra. The SAOC is also designed to recognize and selectively bind to target mRNA sequence, which may correspond to a sequence contained within the sequence shown in SEQ ID NO:1, SEQ ID NO:7 or SEQ ID NO:8. The SAOC is designed to inactivate target mRNA sequence by either binding thereto and inducing degradation of the mRNA by, for example, RNase I digestion, or inhibiting translation of mRNA target sequence by interfering with the binding of translation-regulating factors or ribosomes, or inclusion of other chemical structures, such as ribozyme sequences or reactive chemical groups which either degrade or chemically modify the target mRNA. SAOCs have been shown to be capable of such properties when directed against mRNA targets (see Cohen et al., *TIPS*, 10:435 (1989) and Weintraub, *Sci. American*, January (1990), pp.40; both incorporated herein by reference).

In accordance with yet another embodiment of the present invention, there is provided a method for the recombinant production of invention CHD protein(s) by expressing the above-described nucleic acid sequences in suitable host cells. Recombinant DNA expression systems that are suitable to produce CHD proteins described herein are well-known in the art. For example, the above-described nucleotide sequences can be incorporated into vectors for further manipulation. As used herein, vector (or plasmid) refers to discrete elements that are used to introduce heterologous DNA into cells for either expression or replication thereof.

Suitable expression vectors are well-known in the art, and include vectors capable of expressing DNA operatively linked to a regulatory sequence, such as a promoter region that is capable of regulating expression of such DNA. Thus, an expression vector refers to a recombinant DNA or RNA construct, such as a plasmid, a phage, recombinant virus or other vector that, upon introduction into an appropriate host cell, results in expression of the inserted DNA. Appropriate expression vectors are well known to those of skill in the art and include those that are replicable in eukaryotic cells and/or prokaryotic cells and those that remain episomal or those which integrate into the host cell genome.

As used herein, a promoter region refers to a segment of DNA that controls transcription of DNA to which it is operatively linked. The promoter region includes specific sequences that are sufficient for RNA polymerase recognition, binding and transcription initiation. In addition, the promoter region includes sequences that modulate this recognition, binding and transcription initiation activity of RNA polymerase. These sequences may be cis acting or may be responsive to trans acting factors. Promoters, depending upon the nature of the regulation, may be constitutive or regulated. Exemplary promoters contemplated for use in the practice of the present invention include the SV40 early promoter, the cytomegalovirus (CMV) promoter, the mouse mammary tumor virus (MMTV) steroid-inducible promoter, Moloney murine leukemia virus (MMLV) promoter, and the like.

As used herein, the term "operatively linked" refers to the functional relationship of DNA with regulatory and effector nucleotide sequences, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes, binds to and transcribes the DNA.

As used herein, expression refers to the process by which polynucleic acids are transcribed into mRNA and translated into peptides, polypeptides, or proteins. if the polynucleic acid is derived from genomic DNA, expression may, if an appropriate eukaryotic host cell or organism is selected, include splicing of the mRNA.

Prokaryotic transformation vectors are well-known in the art and include pblueskript and phage Lambda ZAP vectors (Stratagene, La Jolla, Calif.) , and the like. Other suitable vectors and promoters are disclosed in detail in U.S. Pat. No. 4,798,885, issued Jan. 17, 1989, the disclosure of which is incorporated herein by reference in its entirety.

Other suitable vectors for transformation of *E. coli* cells include the pET expression vectors (Novagen, see U.S. Pat. No. 4,952,496), e.g., pET11a, which contains the T7 promoter, T7 terminator, the inducible *E. coli* lac operator, and the lac repressor gene; and pET 12a–c, which contain the T7 promoter, T7 terminator, and the *E. coli* ompT secretion signal. Another suitable vector is the pIN-IIIompA2 (see Duffaud et al., *Meth. in Enzymoloy*, 153:492–507, 1987), which contains the lpp promoter, the lacUV5 promoter operator, the ompA secretion signal, and the lac repressor gene.

Exemplary, eukaryotic transformation vectors, include the cloned bovine papilloma virus genome, the cloned genomes of the murine retroviruses, and eukaryotic cassettes, such as the pSV-2 gpt system [described by Mulligan and Berg, Nature Vol. 277:108–114 (1979)] the Okayama-Berg cloning system [Mol. Cell Biol. Vol. 2:161–170 (1982)], and the expression cloning vector described by Genetics Institute [Science Vol. 228:810–815 (1985)], are available which provide substantial assurance of at least some expression of the protein of interest in the transformed eukaryotic cell line.

Particularly preferred base vectors which contain regulatory elements that can be linked to the invention CHD-encoding DNAs for transfection of mammalian cells are cytomegalovirus (CMV) promoter-based vectors such as pcDNA1 (Invitrogen, San Diego, Calif.), MMTV promoter-based vectors such as pMAMNeo (Clontech, Palo Alto, Calif.) and pMSG (Pharmacia, Piscataway, N.J.), and SV40 promoter-based vectors such as pSVβ (Clontech, Palo Alto, Calif.).

In accordance with another embodiment of the present invention, there are provided "recombinant cells" containing the nucleic acid molecules (i.e., DNA or mRNA) of the present invention. Methods of transforming suitable host cells, preferably bacterial cells, and more preferably *E. coli* cells, as well as methods applicable for culturing said cells containing a gene encoding a heterologous protein, are generally known in the art. See, for example, Sambrook et al., *Molecular Cloning*: A Laboratory Manual (2 ed.), Cold Spring Harbor Laboratory Press, Cold Spring Harbor, N.Y., USA (1989).

Exemplary methods of transformation include, e.g., transformation employing plasmids, viral, or bacterial phage vectors, transfection, electroporation, lipofection, and the like. The heterologous DNA can optionally include sequences which allow for its extrachromosomal maintenance, or said heterologous DNA can be caused to integrate into the genome of the host (as an alternative means to ensure stable maintenance in the host).

Host organisms contemplated for use in the practice of the present invention include those organisms in which recombinant production of heterologous proteins has been carried out. Examples of such host organisms include bacteria (e.g., *E. coli*), yeast (e.g., *Saccharomyces cerevisiae, Candida tropicalis, Hansenula polymorpha* and *P. pastoris*; see, e.g., U.S. Pat. Nos. 4,882,279, 4,837,148, 4,929,555 and 4,855,231), mammalian cells (e.g., HEK293, CHO and Ltk⁻ cells), insect cells, and the like. Presently preferred host organisms are bacteria. The most preferred bacteria is *E. coli*.

In one embodiment, nucleic acids encoding the invention CHD proteins can be delivered into mammalian cells, either in vivo or in vitro using suitable viral vectors well-known in the art. Suitable retroviral vectors, designed specifically for in vivo "gene therapy" methods, are described, for example, in WIPO publications WO 9205266 and WO 9214829, which provide a description of methods for efficiently introducing nucleic acids into human cells in vivo. In addition, where it is desirable to limit or reduce the in vivo expression of the invention CHD, the introduction of the antisense strand of the invention nucleic acid is contemplated.

In accordance with yet another embodiment of the present invention, there are provided anti-CHD antibodies having specific reactivity with CHD polypeptides of the present invention. Active fragments of antibodies are encompassed within the definition of "antibody". Invention antibodies can be produced by methods known in the art using invention polypeptides, proteins or portions thereof as antigens. For example, polyclonal and monoclonal antibodies can be produced by methods well known in the art, as described, for example, in Harlow and Lane, *Antibodies: A Laboratory Manual* (Cold Spring Harbor Laboratory (1988)), which is incorporated herein by reference. Invention polypeptides can be used as immunogens in generating such antibodies. Alternatively, synthetic peptides can be prepared (using commercially available synthesizers) and used as immunogens. Amino acid sequences can be analyzed by methods well known in the art to determine whether they encode hydrophobic or hydrophilic domains of the corresponding polypeptide. Altered antibodies such as chimeric, humanized, CDR-grafted or bifunctional antibodies can also be produced by methods well known in the art. Such antibodies can also be produced by hybridoma, chemical synthesis or recombinant methods described, for example, in Sambrook et al., supra., and Harlow and Lane, supra. Both anti-peptide and anti-fusion protein antibodies can be used. (see, for example, Bahouth et al., *Trends Pharmacol. Sci.* 12:338 (1991); Ausubel et al., *Current Protocols in Molecular Biology* (John Wiley and Sons, N.Y. (1989) which are incorporated herein by reference)

Antibody so produced can be used, inter alia, in diagnostic methods and systems to detect the level of CHD protein present in a mammalian, preferably human, body sample, such as tissue or vascular fluid. Such antibodies can also be used for the immunoaffinity or affinity chromatography purification of the invention CHD protein. In addition, methods are contemplated herein for detecting the presence of CHD polypeptides on the surface of a cell comprising contacting the cell with an antibody that specifically binds to CHD polypeptides, under conditions permitting binding of the antibody to the polypeptides, detecting the presence of the antibody bound to the cell, and thereby detecting the presence of invention polypeptides on the surface of the cell. With respect to the detection of such polypeptides, the antibodies can be used for in vitro diagnostic or in vivo imaging methods.

Immunological procedures useful for in vitro detection of target CHD polypeptides in a sample include immunoassays that employ a detectable antibody. Such immunoassays include, for example, ELISA, Pandex microfluorimetric assay, agglutination assays, flow cytometry, serum diagnostic assays and immunohistochemical staining procedures which are well known in the art. An antibody can be made detectable by various means well known in the art. For example, a detectable marker can be directly or indirectly attached to the antibody. Useful markers include, for example, radionucleotides, enzymes, fluorogens, chromogens and chemiluminescent labels.

Invention anti-CHD antibodies are contemplated for use herein to modulate the activity of the CHD polypeptide in living animals, in humans, or in biological tissues or fluids isolated therefrom. Accordingly, compositions comprising a carrier and an amount of an antibody having specificity for CHD polypeptides effective to block naturally occurring ligands or other CHD-binding proteins from binding to invention CHD polypeptides are contemplated herein. For example, a monoclonal antibody directed to an epitope of CHD polypeptide molecules present on the surface of a cell and having an amino acid sequence substantially the same as an amino acid sequence for a cell surface epitope of an CHD polypeptide including the amino acid sequence shown in SEQ ID NO:2, or the CHD encoding portions of SEQ ID NO:7 or SEQ ID NO:8, can be useful for this purpose.

The present invention further provides transgenic non-human mammals that are capable of expressing exogenous nucleic acids encoding CHD polypeptides. As employed herein, the phrase "exogenous nucleic acid" refers to nucleic acid sequence which is not native to the host, or which is present in the host in other than its native environment (e.g., as part of a genetically engineered DNA construct).

Also provided are transgenic non-human mammals capable of expressing nucleic acids encoding CHD polypeptides so mutated as to be incapable of normal activity, i.e., do not express native CHD. The present invention also provides transgenic non-human mammals having a genome comprising antisense nucleic acids complementary to nucleic acids encoding CHD polypeptides, placed so as to be transcribed into antisense mRNA complementary to mRNA encoding CHD polypeptides, which hybridizes to the mRNA and, thereby, reduces the translation thereof. The nucleic acid may additionally comprise an inducible promoter and/or tissue specific regulatory elements, so that expression can be induced, or restricted to specific cell types. Examples of nucleic acids are DNA or cDNA comprising a coding sequence substantially the same as the coding sequence shown in SEQ ID NO:1, SEQ ID NO:7 or SEQ ID NO:8. An example of a non-human transgenic mammal is a transgenic mouse. Examples of tissue specificity-determining elements are the metallothionein promoter and the L7 promoter.

Animal model systems which elucidate the physiological and behavioral roles of CHD polypeptides are also provided, and are produced by creating transgenic animals in which the expression of the CHD polypeptide is altered using a variety of techniques. Examples of such techniques include the insertion of normal or mutant versions of nucleic acids encoding an CHD polypeptide by microinjection, retroviral infection or other means well known to those skilled in the art, into appropriate fertilized embryos to produce a transgenic animal. (See, for example, Hogan et al., *Manipulating the Mouse Embryo: A Laboratory Manual* (Cold Spring Harbor Laboratory, (1986)).

Also contemplated herein, is the use of homologous recombination of mutant or normal versions of CHD genes with the native gene locus in transgenic animals, to alter the regulation of expression or the structure of CHD polypeptides (see, Capecchi et al., *Science* 244:1288 (1989); Zimmer et al., *Nature* 338:150 (1989); which are incorporated herein by reference). Homologous recombination techniques are well known in the art. Homologous recombination replaces the native (endogenous) gene with a recombinant or mutated gene to produce an animal that cannot express native (endogenous) protein but can express, for example, a mutated protein which results in altered expression of CHD polypeptides.

In contrast to homologous recombination, microinjection adds genes to the host genome, without removing host genes. Microinjection can produce a transgenic animal that is capable of expressing both endogenous and exogenous CHD protein. Inducible promoters can be linked to the coding region of nucleic acids to provide a means to regulate expression of the transgene. Tissue specific regulatory elements can be linked to the coding region to permit tissue-specific expression of the transgene. Transgenic animal model systems are useful for in vivo screening of compounds for identification of specific ligands, i.e., agonists and antagonists, which activate or inhibit protein responses.

Invention nucleic acids, oligonucleotides (including antisense), vectors containing same, transformed host cells, polypeptides and combinations thereof, as well as antibodies of the present invention, can be used to screen compounds in vitro to determine whether a compound functions as a potential agonist or antagonist to invention polypeptides. These in vitro screening assays provide information regarding the function and activity of invention polypeptides, which can lead to the identification and design of compounds that are capable of specific interaction with one or more types of polypeptides, peptides or proteins.

In accordance with still another embodiment of the present invention, there is provided a method for identifying compounds which bind to CHD polypeptides. The invention proteins may be employed in a competitive binding assay. Such an assay can accommodate the rapid screening of a large number of compounds to determine which compounds, if any, are capable of binding to CHD proteins. Subsequently, more detailed assays can be carried out with those compounds found to bind, to further determine whether such compounds act as modulators, agonists or antagonists of invention proteins.

In another embodiment of the invention, there is provided a bioassay for identifying compounds which modulate the activity of invention polypeptides. According to this method, invention polypeptides are contacted with an "unknown" or test substance (in the presence of a reporter gene construct when antagonist activity is tested), the activity of the polypeptide is monitored subsequent to the contact with the "unknown" or test substance, and those substances which cause the reporter gene construct to be expressed are identified as functional ligands for CHD polypeptides.

In accordance with another embodiment of the present invention, transformed host cells that recombinantly express invention polypeptides can be contacted with a test compound, and the modulating effect(s) thereof can then be evaluated by comparing the CHD-mediated response (e.g., via reporter gene expression) in the presence and absence of test compound, or by comparing the response of test cells or control cells (i.e., cells that do not express CHD polypeptides), to the presence of the compound.

As used herein, a compound or a signal that "modulates the activity" of invention polypeptides refers to a compound or a signal that alters the activity of CHD polypeptides so that the activity of the invention polypeptide is different in the presence of the compound or signal than in the absence of the compound or signal. In particular, such compounds or signals include agonists and antagonists. An agonist encompasses a compound or a signal that activates CHD protein expression. Alternatively, an antagonist includes a compound or signal that interferes with CHD protein expression. Typically, the effect of an antagonist is observed as a blocking of agonist-induced protein activation. Antagonists include competitive and non-competitive antagonists. A competitive antagonist (or competitive blocker) interacts with or near the site specific for agonist binding. A non-competitive antagonist or blocker inactivates the function of the polypeptide by interacting with a site other than the agonist interaction site.

As understood by those of skill in the art, assay methods for identifying compounds that modulate CHD activity generally require comparison to a control. One type of a "control" is a cell or culture that is treated substantially the same as the test cell or test culture exposed to the compound, with the distinction that the "control" cell or culture is not exposed to the compound. For example, in methods that use voltage clamp electrophysiological procedures, the same cell can be tested in the presence or absence of compound, by merely changing the external solution bathing the cell. Another type of "control" cell or culture may be a cell or culture that is identical to the transfected cells, with the exception that the "control" cell or culture do not express native proteins. Accordingly, the response of the transfected cell to compound is compared to the response (or lack thereof) of the "control" cell or culture to the same compound under the same reaction conditions.

In yet another embodiment of the present invention, the activation of CHD polypeptides can be modulated by contacting the polypeptides with an effective amount of at least one compound identified by the above-described bioassays.

In accordance with another embodiment of the present invention, there are provided methods for diagnosing Down Syndrome-CHD, said method comprising: detecting, in said subject, a genomic or transcribed mRNA sequence including SEQ ID NO:1, SEQ ID NO:7 or SEQ ID NO:8.

In accordance with another embodiment of the present invention, there are provided diagnostic systems, preferably in kit form, comprising at least one invention nucleic acid in a suitable packaging material. The diagnostic nucleic acids are derived from the CHD-encoding nucleic acids described herein. In one embodiment, for example, the diagnostic nucleic acids are derived from SEQ ID NO:1. Invention diagnostic systems are useful for assaying the presence or absence of nucleic acid encoding CHD in either genomic DNA or in transcribed nucleic acid (such as mRNA or cDNA) encoding CHD.

A suitable diagnostic system includes at least one invention nucleic acid, preferably two or more invention nucleic acids, as a separately packaged chemical reagent(s) in an amount sufficient for at least one assay. Instructions for use of the packaged reagent are also typically included. Those of skill in the art can readily incorporate invention nucleic acid probes and/or primers into kit form in combination with appropriate buffers and solutions for the practice of the invention methods as described herein.

As employed herein, the phrase "packaging material" refers to one or more physical structures used to house the contents of the kit, such as invention nucleic acid probes or primers, and the like. The packaging material is constructed by well known methods, preferably to provide a sterile, contaminant-free environment. The packaging material has a label which indicates that the invention nucleic acids can be used for detecting a particular sequence encoding CHD including the nucleotide sequence set forth in SEQ ID NO:1, SEQ ID NO:7 or SEQ ID NO:8, thereby diagnosing the presence of, or a predisposition for, Down Syndrome congenital heart disease (DS-CHD). In addition, the packaging material contains instructions indicating how the materials within the kit are employed both to detect a particular sequence and diagnose the presence of, or a predisposition for, Down Syndrome congenital heart disease (DS-CHD).

The packaging materials employed herein in relation to diagnostic systems are those customarily utilized in nucleic acid-based diagnostic systems. As used herein, the term "package" refers to a solid matrix or material such as glass, plastic, paper, foil, and the like, capable of holding within fixed limits an isolated nucleic acid, oligonucleotide, or primer of the present invention. Thus, for example, a package can be a glass vial used to contain milligram quantities of a contemplated nucleic acid, oligonucleotide or primer, or it can be a microtiter plate well to which microgram quantities of a contemplated nucleic acid probe have been operatively affixed.

"Instructions for use" typically include a tangible expression describing the reagent concentration or at least one assay method parameter, such as the relative amounts of reagent and sample to be admixed, maintenance time periods for reagent/sample admixtures, temperature, buffer conditions, and the like.

All U.S. patents and all publications mentioned herein are incorporated in their entirety by reference thereto. The invention will now be described in greater detail by reference to the following non-limiting examples.

The invention will now be described in greater detail by reference to the following non-limiting examples. All U.S. patents and all publications mentioned herein are incorporated in their entirety by reference thereto.

Unless otherwise stated, the present invention was performed using standard procedures, as described, for example in Maniatis et al., *Molecular Cloning: A Laboratory Manual*, Cold Spring Harbor Laboratory Press, Cold Spring Harbor, N.Y., USA (1982) ; Sambrook et al., *Molecular Cloning*: A Laboratory Manual (2 ed.), Cold Spring Harbor Laboratory Press, Cold Spring Harbor, N.Y., USA (1989); Davis et al., *Basic Methods in Molecular Biology*, Elsevier Science Publishing, Inc., New York, USA (1986); or *Methods in Enzymology: Guide to Molecular Cloning Techniques* Vol.152, S. L. Berger and A. R. Kimmerl Eds., Academic Press Inc., San Diego, USA (1987).

Materials and Methods

Unless otherwise stated, the present invention was performed using standard procedures, as described, for example in Maniatis et al., *Molecular Cloning: A Laboratory Manual*, Cold Spring Harbor Laboratory Press, Cold Spring Harbor, N.Y., USA (1982); Sambrook et al., *Molecular Cloning: A Laboratory Manual* (2 ed.), Cold Spring Harbor Laboratory Press, Cold Spring Harbor, N.Y., USA (1989); Davis et al., *Basic Methods in Molecular Biology*, Elsevier Science Publishing, Inc., New York, USA (1986); or *Methods in Enzymology: Guide to Molecular Cloning Techniques* Vol.152, S. L. Berger and A. R. Kimmerl Eds., Academic Press Inc., San Diego, USA (1987)).

Libraries. Yeast artificial chromosome (YAC) clones were obtained from the CEPH mega-YAC library and grown under standard conditions (Cohen et al., Nature 366:689–701 (1993)). P1 artificial chromosome (PAC) library construction. A 3× human PAC library, designated RPCI-1 (Ioannou et al., *Hum. Genet.* 219–220 (1994b)) was constructed as described (Ioannou et al., *Nat. Genet.* 6:84–89 (1994a)). The library was arrayed in 384 well dishes. Subsequently, STSs generated by sequencing of clones using vector primers were used as hybridization probes to gridded colony filters of the PAC library.

YAC DNA preparation. YAC clones were grown in selective media, pelleted and resuspended in 3 ml 0.9 M sorbitol, 0.1M EDTA pH 7.5, then incubated with 100 U of lytocase (Sigma) at 37° C. for 1 hour. After centrifugation for 5 minutes at 5,000 rpm pellets were resuspended in 3 ml 50 mM Tris pH 7.45, 20 mM EDTA three-tenth ml 10% SDS was added and the mixture was incubated at 65° C. for 30 minutes. One ml of 5 M potassium acetate was added and tubes were left on ice for 1 hour, then centrifuged at 10,000 rpm for 10 minutes. Supernatant was precipitated in 2 volumes of ethanol and pelleted at 6,000 rpm for 15 minutes. Pellets were resuspended in TE, treated with RNase and reextracted with phenol-chloroform.

Analysis by pulsed-field gel electrophoresis. Agarose plugs of yeast cells containing total YAC DNA were prepared (Larin and Lehrach, *Genet. Rcs.* 56:203–208 (1990)) and subjected to pulsed-field gel separation on 1% SeaKem agarose gels in 0.5× TBE using the CHEF DRII Mapper (Bio-Rad). PAC and BAC clones were sized after digestion with NotI. Gels were blotted onto Magna NT Nylon membranes using alkaline blotting, UV cross linked and baked at 80° C. for two hours. The sizes of individual clones were determined by comparison to their relative positions with molecular weight standards.

Analysis by fluorescence in situ hybridization (FISH). PAC or BAC clones were biotinylated by nicktranslation in the presence of biotin-14-dATP using the BioNick Labeling Kit (Gibco-BRL). FISH was performed essentially as described (Korenberg et al., *Cytogenet Cell Genet*. 69:196–200 (1995)). Briefly, 400 ng of probe DNA was mixed with 8 ng of human Cot 1 DNA (Gibco-BRL) and 2 ug of sonicated salmon sperm DNA in order to suppress possible background produced from repetitive human sequences as well as yeast sequences in the probe. The probes were denatured at 75° C., preannealed at 37° C. for one hour, and applied to denatured chromosome slides prepared from normal male lymphocytes (Korenberg et al., 1995, supra). Post-hybridization washes were performed at 40° C. in 2× SSC/50% formamide followed by washes in 1× SSC at 50° C. Hybridized DNAs were detected with avidin-conjugated fluorescent isothiocyanate (Vector Laboratories). One amplification was performed by using biotinylated anti-avidin. For distinguishing chromosome subbands precisely, a reverse banding technique was used, which was achieved by chromomycin A3 and distamycin A double staining (Korenberg et al., 1995, supra). The color images were captured by using a Photometrics Cooled-CCD camera and BDS image analysis software (Oncor Imaging, Inc.).

PAC and BAC DNA preparation. Selected clones were grown overnight in LB media containing 12.5 $\mu$g/ml kanamycin for PACs and 12.5 $\mu$g/ml chloramphenicol for BACs. DNAs were prepared by the alkaline lysis method. BAC and PAC DNAs were digested with NotI and subjected to pulsed-field gel electrophoresis. Sizes were determined relative to $\lambda$ concatamers.

Southern blot analysis. Gel electrophoresis of DNA was carried out on 0.8% agarose gels in 1× TBE. Transfer of nucleic acids to Nybond N+ nylon membrane (Amersham) was performed according to the manufacturer's instruction. Probes were labeled using RadPrime Labeling System (BRL). Hybridization was carried out at 42° C. for 16 hours in 50% formamide, 5× SSPE, 5× Denhardt's 0.1% SDS, 100 mg/ml denatured salmon sperm DNA. The filters were washed once in 1× SSC, 0.1% SDS at room temperature for 20 minutes, and twice in 0.1× SSC, 0.1% SDS for 20 minutes at 65° C. The blots were exposed onto X-ray film (Kodak, X-OMAT-AR).

Sequencing of PAC and BAC endclones. PAC clones were inoculated into 500 ml of LB/kanamycin and grown overnight. BAC clones were inoculated into 500 ml of LB/chloramphenicol and grown overnight. DNAs were isolated using QIAGEN columns according to the vendors protocol with one additional phenol/chloroform/isoamylalcohol extraction followed by one additional chloroform/isoamylalcohol extraction. Clones were sequenced using the Gibco-BRL cycle sequencing kit with standard T7 and SP6 primers.

EXAMPLE 1

Construction of BAC Contig

To provide stable clones for gene isolation and sequencing initiatives in the D21S55 to MX1 region, we constructed contigs using Bacterial Artificial Chromosomes (BACs) and P1 Artificial Chromosomes (PACs). BAC library construction of total human genomic DNA was performed as described in Shizuya et al., *Proc. Natl. Acad. Sci. USA* 8:8794–8797 (1992). A BAC library was screened using several YACs spanning the region; a PAC library was screened using radiolabeled STS PCR products and whole BACs in gap filling initiatives.

The location of these BAC and PAC clones was confirmed by fluorescence in-situ hybridization (FISH). Clone to clone Southerns using 24 new STSs (generated from the direct sequencing of BAC and PAC ends) along with 35 pre-existing STSs were used show overlaps between BACs and PACs. The STS density over the intervals covered in BACs and PACs was 1 STS every 60 kb, and 79% of the clones were positive for 2 or more STSs. Approximately 3.5 Mb of the 4–5 Mb D21S55 to MX1 interval is covered in 85 BACs and 25 PACs representing 4 fold coverage within the contigs. The minimal contig sizes as determined by counting only non-overlapping clones are: 1100 kb, 900 kb, 510 kb, 380 kb and 270 kb. Insert size of BAC clones was measured by running pulsed-field gel electrophoresis after digesting DNA with NotI.

EXAMPLE 2

Direct cDNA Selection

Direct selection procedures were similar to those described in Morgan et al., *Nucleic Acid Res*. 20:5173–5179 (1992) with some modifications. Total RNA was isolated from 14 week trisomy 21 fetal brain using TRI region™ (Molecular Research Center, Inc.). Poly (A)$^+$ RNA was isolated using Poly (A) Quick® mRNA isolation kit (STRATAGENE). Double stranded cDNA was synthesized using SuperScript™ Choice System (GIBCO BRL) from 5 $\mu$g trisomy 21 fetal brain poly (A)$^+$ RNA using 1 $\mu$g oligo (dT)$_{15}$ or 0.1 $\mu$g random hexamer. The entire synthesis reaction was purified by Gene Clean®II kit (BIO101, Inc.) and then kinased. Sau3AI linker was attached to the cDNA which was subsequently digested with Sau3AI. The reaction was purified using Gene Clean. MboI linker was attached to the cDNA and the reaction purified by Gene Clean (Morgan et al., *Nucleic Acid Res*. 2:5173–5179 (1992)). The synthesized product was amplified by PCR using one strand of MboI linker (5'CCTGATGCTCGAGTGAATTC3') (SEQ ID NO:4) as a primer. PCR cycling conditions were 40 cycles of 94° C./15 seconds, 60° C./23 seconds, 72° C./2 minutes in a 100 $\mu$l of 1× PCR buffer (Promega), 3 mM MgCl$_2$, 5.0 units of Taq polymerase (Promega), 2 $\mu$M primer and 0.2 mM dNTPs.

Nineteen BAC DNAs (total 2.5 $\mu$g) and 2 PAC DNAs between the region ETS2 and MX1 were prepared using QIAGEN plasmid kit and were biotinylated using Nick Translation Kit and biotin-16-dUTP (Boehringer Manneheim). 3 $\mu$g of heat denatured PCR amplified cDNA was annealed with 3 $\mu$g of heat denatured COT1 DNA (BRL) in 100 $\mu$l hybridization buffer (750 mM NaCl, 50 mM NaPO$_4$(pH7.2), 5 mM EDTA, 5× Denhardt's, 0.05% SDS and 50% formamide) at 42° C. for two hours. After prehybridization, 1.2 $\mu$g of heat denatured biotinylated BAC DNA was added and incubated at 42° C. for 16 hours. cDNA-BAC DNA hybrids were precipitated with EtOH and dissolved in 60 $\mu$l of 10 mM Tris-HCl (pH 8.0), 1 mM EDTA. After addition of 40 $\mu$l 5M NaCl, the DNA was incubated with magnetic beads (Dynabeads M-280, Dynal) at 25° C. for 1 hour with gentle rotating to allow attachment of the DNA to the magnetic beads. The beads were then washed twice by pipetting in 400 $\mu$l of 2× SSC, setting in magnet holder (MPC-E™, Dynal) for 30 seconds and removing the supernatant. Four additional washes were performed in 0.2× SSC at 68° C. for 10 minutes each with transfer of the beads to new tubes at each wash. cDNAs were eluted in 100 μl of distilled water for 10 minutes at 80° C. with occasional mixing. The eluted cDNAs were amplified by PCR as described above. After twice repeating the selection procedure using magnetic beads, amplified cDNAs were digested with EcoRI and subcloned into pBluescript II.

The direct cDNA selection procedure using 19 BACs and 2 PACs between ETS2 and MX1 generated a total of 145 unique cDNA fragments. Genbank and TIGR homology searches using FASTA revealed matches to ETS2, HMG14, PEP19, a Na K ATPase, Titan ESTs, MX1 region ESTs, and 14 ESTs of unknown function. A cDNA library from a trisomy 21 fetal brain at 14 weeks gestation was screened using one of these unique cDNA fragments labelled "A64".

EXAMPLE 3

Isolation of Human CHD cDNA Using cDNA Library Screening

A trisomy 21 fetal brain cDNA library was constructed using ZAP-cDNA® synthesis kit (STRATAGENE) which generates a unidirectional cDNA library. Briefly, double-stranded cDNA was synthesized from 5 μg trisomy 21 fetal brain poly(A)$^+$ RNA using a hybrid oligo(dT)-XhoI linker primer with 5-methyl dCTP. An EcoRI linker was attached to the cDNA which was subsequently digested with EcoRI and XhoI, and then cloned into UNI-ZAP XR vector. The library was packaged using Gigapack® II Gold packaging extract. The titer of the original library was $1.1 \times 10^6$ p.f.u./package. The library was amplified once. A blue-white color assay indicated that 99% of the clones had inserts. The average size of the inserts was 1.9 kb, as calculated from 14 clones.

Screening of the trisomy 21 fetal brain cDNA library was performed using one of the 145 unique cDNA fragments labelled "A64" (SEQ ID NO:3) prepared as discussed above. Phages were plated to an average density of $1 \times 10^5$ per 175 cm$^2$ plate. Plaque lifts of 20 plates ($2 \times 10^6$ phages) were made using duplicated nylon membranes (Hybond-N+; Amersham). Hybridized membranes were washed to final stringency of 0.2× SSC, 0.1× SDS at 65° C. The filters were exposed overnight onto X-ray film. Phages were subcloned into the plasmid vector pBluescript II SK(−) by M13-mediated excision for further analysis. A cDNA clone encoding a novel protein labelled "CHD" was isolated. The cDNA encoding CHD has at least an 864 base pair open reading frame (SEQ ID NO:1) coding for a 288 amino acid sequence (SEQ ID NO:2).

EXAMPLE 4

Northern Blot Analysis Of Human CHD Expression

Inserts containing CHD cDNA were excised from the base vector by digestion with XhoI and EcoRI. After labeling using the random priming method, the fragments were used a probes for Northern hybridization using Multiple Tissue Northern Blot (Clontech). A Northern blot assay was conducted using CHD cDNA as a probe in various tissues including adult heart, brain, placenta, lung, liver, skeletal muscle, kidney, and pancreas. The results reveal expression primarily in adult heart and skeletal muscle with lower level ubiquitous expression. Brain, placenta, lung, liver, kidney and pancreas show very little expression of CHD. The major transcript observed on the Northern blot in the heart tissue is 2.4 kb in size while the major transcript in muscle is at 1.2 kb. Heart has a minor transcript around 1.2 kb and skeletal muscle has a minor transcript at 2.6 kb. Thus, splice variant cDNA transcripts encoding a CHD family of proteins are clearly contemplated by the present invention.

EXAMPLE 5

RT-PCR Assays Of Human CHD Expression

Reverse-transcriptase polymerase chain reaction (RT-PCR) assays verses cDNA libraries of various human tissues were conducted using primers numbered CHD-31 (SEQ ID NO:5) and CHD-52 (SEQ ID NO:6). The results demonstrated expression of human CHD mRNA in the day 53 and day 55 human fetal heart and in the 6–9 week heart. The temporal and tissue specific expression patterns of CHD further support the association of CHD with DS-CHD.

EXAMPLE 6

Isolation of Mouse CHD cDNA

Mouse homologs of CHD were isolated using the 1053 base pair human cDNA clone (SEQ ID NO:1) as a probe to screen a mouse brain cDNA library. Double stranded cDNA was synthesized from 5 μg of mouse brain poly(A)$^+$ RNA isolated from female C57 Black/6 mice at 19 weeks of age. The cDNA was oligo(dT) primed using a hybrid oligo(dT)-XhoI linker primer with 5-methyl dCTP. An EcoRI linker was ligated to the cDNA, the cDNA was digested with EcoRI and XhoI, and cloned into the UniZAP XR vector (STRATAGENE; Catalog #937314). The average insert size of the library was 1.0 kb.

Screening of the library was done by filter hybridization as described in EXAMPLE 3 using the human CHD cDNA (SEQ ID NO:1) as a probe. Forty positive clones were identified by screening $2 \times 10^6$ clones in the library. Analysis of one of the mouse clones, designated CHD1-Mos-3 revealed a ~1.0 kb cDNA. The partial cDNA sequences of the CHD-1-Mos-3 clone corresponding to the 5' region and the 3' region are set forth in SEQ ID NO:7 and SEQ ID NO:8, respectively. The identity of the 416 base pair 5' end (SEQ ID NO:7) of the mouse cDNA to the human CHD clone (SEQ ID NO:1) was 81%. In addition, the sequence analysis of the mouse CHD-1-Mos-3 cDNA revealed 77.5% identity with the human CHD clone (SEQ ID NO:1) in a 320 base pair overlapping sequence at the 3' end (SEQ ID NO:8) of the mouse cDNA.

EXAMPLE 7

In Situ Characterization of Mouse CHD Expression

To further examine the expression of mouse CHD, tissue in situ hybridization analysis was performed by using the mouse CHD-1-Mos-3 cDNA as a probe on sections of normal mouse embryos from days 7.5.5–17.5 post-coitum, newborn mice, mice at two weeks of age and adult brains.

The BALB/c and C57BL/6×DBA/2 embryos, fetuses and postnatal brains were fixed in 4% paraformaldehyde in phosphate buffered saline (PBS) overnight, dehydrated and infiltrated with paraffin. Serial sections of five to seven microns were mounted on gelatinized slides. Two sections were mounted per slide, deparaffinized in xylene, rehydrated and post-fixed. The sections were digested with proteinase K, post-fixed, treated with tri-ethanolamine/acetic anhydride, washed and dehydrated. The cRNA probes were prepared from the mouse CHD-1-Mos-3 cDNA. The plasmid was linearized with KpnI and T3 polymerase was used to generate the sense control cRNA. The cRNA transcripts were synthesized according to manufacturer's conditions (STRATAGENE) and labeled with $^{35}$S-UTP (>1000 Ci/mmol; AMERSHAM). The cRNA transcripts larger than 100 nucleotides were subjected to alkali hydrolysis to give a mean size of 70 bases for efficient hybridization. Sections were hybridized overnight at 52° C. in 50% deionized formamide, 0.3 M sodium chloride, 20 mM Tris-Hcl, pH 7.4, 5 mM EDTA, 10 mM NaPO$_4$, 10% dextran sulfate, 1× Denhardt's solution, 50 μg/ml of total yeast RNA and 50–75,000 cpm/ml of $^{35}$S-labeled cRNA probe. The tissue was subjected to stringent washing at 65° C. in 50% formamide, 2× SSC, 10 mM dithiothreitol and washed in PBS before treatment with 20 μg/ml RNase A at 37° C. for 30 minutes. Following washes in 2× SSC and 0.1× SSC for ten minutes at 37° C., the slides were dehydrated and dipped in Kodak NTB-2 nuclear track emulsion and exposed for two to three weeks in light-tight boxes with desiccant at 4° C. Photographic development was carried out in Kodak D-19. Slides were counterstained lightly with toluidine blue and analyzed using both light- and darkfield optics of a Zeiss Axiphot microscope. Sense control cRNA probes are identical to the mRNAs in the cells and always give background levels of hybridization signal. Embryonic structures were identified using well-known atlases.

The results indicate that the mouse CHD-1-Mos-3 clone is highly expressed in all embryonic cells from days 7.5 to 9.5 post coitum. At 10.5 days, the mouse CHD-1-Mos-3 expression decreases in some tissues and organs, but remains prominent in others. For example, higher levels of expression appear in the lung, liver and mandibular arch. Expression also appears higher in caudal regions such as hind limbbuds compared to more rostral neural tube and surrounding mesenchyme. At 11.5 days, mouse CHD-1-Mos-3 expression is low in the heart, neuroepithelium, cranial ganglia, skeletal muscle and gut. Expression at 11.5 days was highest in the liver. At 12.5 days, the signal in the gut becomes localized to the epithelial lining. The signal that was in the mandibular arch becomes localized predominantly to the tongue muscle. At 13.5 days, mouse CHD-1-Mos-3 levels are highest in the liver and also detected in the kidneys. At 14.5 and 15.5 days, central nervous system expression is highest in the neocortex. In situ hybridization signal in the thymus is equal or higher that of the liver. In the 17.5 day mouse, CHD-1-Mos-3 expression levels are highest in brown fat.

While the invention has been described in detail with reference to certain preferred embodiments thereof, it will be understood that modifications and variations are within the spirit and scope of that which is described and claimed.

Summary of Sequences

SEQ ID NO:1 is the nucleic acid sequence (and the deduced amino acid sequence) of cDNA encoding a human CHD protein of the present invention.

SEQ ID NO:2 is the deduced amino acid sequence of a human CHD protein of the present invention.

SEQ ID NO:3 is the cDNA probe (labeled "A64") used to isolate cDNA encoding CHD.

SEQ ID NO:4 is an MboI linker sequence.

SEQ ID NO:5 is a primer numbered CHD-31 used in the RT-PCR assay described in Example 5.

SEQ ID NO:6 is a primer numbered CHD-52 used in the RT-PCR assay described in Example 5.

SEQ ID NO:7 is a partial sequence of the 5' region of mouse cDNA clone CHD-1-Mos-3 encoding a mouse CHD protein. The putative start codon occurs at nucleotide 281 of SEQ ID NO:7.

SEQ ID NO:8 is a partial sequence of the 3' prime region of mouse cDNA clone CHD-1-Mos-3 encoding a mouse CHD protein. The putative stop codon occurs at nucleotide 316 of SEQ ID NO:8.

That which is claimed is:

1. An isolated polynucleotide comprising a nucleotide sequence set forth in SEQ ID NO: 1, SEQ ID NO:7 or SEQ ID NO:8.

2. An isolated polynucleotide comprising a nucleotide sequence that:
   (a) encodes the amino acid sequence set forth in SEQ ID NO: 2, or the CHD protein encoding portions of SEQ ID NO:7 or SEQ ID NO:8, or
   (b) is degenerate with respect to the nucleotide sequence of (a); or
   (c) a nucleotide sequence that is complementary to the nucleotide sequences of (a) or (b).

3. An isolated first polynucleotide that:
   (i) hybridizes to a second polynucleotide consisting of a nucleotide sequence set forth in SEQ ID NO:1, SEQ ID NO:7 or SEQ ID NO:8 under conditions comprising hybridizing in a first buffer consisting essentially of 50% formamide, 5× Denhardt's solution, 5× SSPE, 0.2% SDS, at 42° C. for a time sufficient to allow formation of stable hybrids, and washing in a second buffer consisting essentially of 0.1× SSPE, 0.1% SDS at 65° C.; and
   (ii) encodes a protein that binds immunospecifically to an antibody, said antibody having immunosrecific reactivity to a protein having the amino acid sequence set forth in SEQ ID NO:2.

4. An isolated first polynucleotide that:
   (i) hybridizes to a second polynucleotide encoding (a) the amino acid sequence set forth in SEQ ID NO:2, or (b) the CHD protein encoding portions of SEQ ID NO:7 or SEQ ID NO:8 under conditions comprising hybridizing in a first buffor consisting essentially of 50% formamide, 5× Denhardt's solution, 5× SSPE, 0.2% SDS, at 42° C. for a time sufficient to allow formation of stable hybrids, and washing in a second buffer consisting essentially of 0.1× SSPE, 0.1% SDS at 65° C.; and
   (ii) encodes a protein that binds immunospecifically to an antibody, said antibody having immunospecific reactivity to a protein having the amino acid sequence set forth in SEQ ID NO:2.

5. The isolated first polynucleotide according to claim 3, wherein the first polynucleotide comprises a nucleotide sequence that (i) is a splice variant of a gene that encodes a protein comprising the amino acid sequence set forth in SEQ ID NO:2; and (ii) is about 1.2 kb, about 2.4 kb, or about 2.6 kb in length.

6. The polynucleotide according to claim 1, 2, 3, 4, or 5, wherein said polynucleotide is cDNA.

7. A vector containing the polynucleotide of claim 1, 2, 3, 4, or 5.

8. A recombinant cell containing the polynucleotide of claim 1, 2, 3, 4, or 5.

9. The polynucleotide according to claim 1, 2, 3, 4, or 5, wherein said polynucleotide is genomic DNA.

10. The polynucleotide according to claim 1, 2, 3, 4, or 5, wherein said polynucleotide is RNA.

11. The recombinant cell according to claim 8 which is a prokaryotic cell.

12. The recombinant cell according to claim 8 which is a eukaryotic cell.

13. A method for preparing a CHD protein comprising culturing the recombinant cell of claim 11 under conditions suitable for expression of said CHD protein, and recovering said CHD protein.

14. A method for preparing a CHD protein comprising culturing the recombinant cell of claim 12 under conditions suitable for expression of said CHD protein, and recovering said CHD protein.

15. An isolated first polynucleotide that:
   (i) hybridizes to a second polynucleotide consisting of a nucleotide sequence set forth in SEQ ID NO:7 under conditions comprising hybridizing in a first buffer consisting essentially of 50% formamide, 5× Denhardt's solution, 5× SSPE, 0.2% SDS, at 42 ° C. for a time sufficient to allow formation of stable hybrids, and washing in a second buffer consisting essentially of 0.1× SSPE, 0.1% SDS at 65° C.; and
   (ii) encodes a polypeptide that binds immunospecifically to an antibody, said antibody having immunospecific reactivity to a protein having the amino acid sequence of SEQ ID NO:2.

16. An isolated first polynucleotide that:
   (i) hybridizes to a second polynucleotide encoding (a) the amino acid sequence set forth in SEQ ID NO:2, or (b) the CHD protein encoding portions of SEQ ID NO:7 under conditions comprising hybridizing in a first buffer consisting essentially of 50% formamide, 5× Denhardt's solution, 5× SSPE, 0.2% SDS, at 42° C. for a time sufficient to allow formation of stable hybrids, and washing in a second buffer consisting essentially of 0.1× SSPE, 0.1% SDS at 65° C.; and
   (ii) encodes a polypeptide that binds immunospecifically to an antibody, said antibody having immunospecific reactivity to a protein having the amino acid sequence of SEQ ID NO:2.

17. A vector containing the polynucleotide of claim 15 or 16.

18. A recombinant cell containing the polynucleotide of claim 15 or 16.

19. A method for preparing a polypeptide that binds immunospecifically to an antibody having immunospecific reactivity to a protein having the amino acid sequence of SEQ ID NO:2, comprising culturing the recombinant cell of claim 18 under conditions suitable for expression of said polypeptide, and recovering said polypeptide.

20. An isolated first polynucleotide that:
   (i) hybridizes to a second polyntcleotide consisting of a nucleotide sequence set forth in SEQ ID NO:1, SEQ ID NO:7 or SEQ ID NO:8, under conditions comprising hybridizing in a first buffer consisting essentially of 50% formamide, 5× Denhardt's solution, 5× SSPE, 0.2% SDS, at 42° C. for a time sufficient to allow formation of stable hybrids, and washing in a second buffer consisting essentially of 0.1× SSPE, 0.1% SDS at 65° C.;
   (ii) encodes a polypeptide that binds immunospecifically to an antibody, said antibody having immunospecific reactivity to a protein having the amino acid sequence set forth in SEQ ID NO:2; and
   (iii) is derived from humans.

21. An isolated first polynucleotide that:
   (i) hybridizes to a second polynucleotide encoding (a) the amino acid sequence set forth in SEQ ID NO:2, or (b) the CHD protein encoding portions of SEQ ID NQ:7 or SEQ ID NO:8, under conditions comprising hybridizing in a first buffer consisting essentially of 50% formamide, 5× Denhardt's solution, 5× SSPE, 0.2% SDS, at 42° C. for a time sufficient to allow formation of stable hybrids, and washing in a second buffer consisting essentially of 0.1× SSPE, 0.1% SDS at 65° C.;
   (ii) encodes a polypeptide that binds iimmunospecifically to an antibody, said antibody having immunospecific reactivity to a protein having the amino acid sequence set forth in SEQ ID NO:2; and
   (iii) is derived from humans.

22. A vector containing the polynucleotide of claim 20 or 21.

23. A recombinant cell containing the polynucleotide of claim 20 or 21.

24. A method for preparing a polypeptide that binds immunospecifically to an antibody having immunospecific reactivity to a protein having the amino acid sequence set forth in SEQ ID NO:2, comprising culturing the recombinant cell of claim 23 under conditions suitable for expression of said polypeptide, and recovering said polypeptide.

* * * * *

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 1053 base pairs
      (B) TYPE: nucleic acid
      (C) STRANDEDNESS: both
      (D) TOPOLOGY: both    (ii) MOLECULE TYPE: cDNA    (ix) FEATURE:
      (A) NAME/KEY: CDS
      (B) LOCATION: 39..905
      (D) OTHER INFORMATION: /product= "CHD PROTEIN"

(xi) SEQUENCE DESCRIPTION: SEQ ID NO:1:

```
CGGCGCTGCA GTTGTGTCCA GCCGGTCACG GGGCGGCT ATG GCG GCC ACG TTC          53
                                        Met Ala Ala Thr Phe
                                          1               5

TTC GGA GAG GTG GTG AAG GCG CCG TGC CGA GCT GGG ACT GAG GAC GAA       101
Phe Gly Glu Val Val Lys Ala Pro Cys Arg Ala Gly Thr Glu Asp Glu
         10                  15                  20
```

-continued

| | |
|---|---|
| GAG GAG GAG GAG GAG GGG CGG AGG GAG ACG CCC GAG GAC AGG GAG GTG<br>Glu Glu Glu Glu Glu Gly Arg Arg Glu Thr Pro Glu Asp Arg Glu Val<br>                25                              30                            35 | 149 |
| CGT CTG CAG CTG GCG CGG AAG AGG GAA GTG CGG CTC CTT CGA AGA CAA<br>Arg Leu Gln Leu Ala Arg Lys Arg Glu Val Arg Leu Leu Arg Arg Gln<br>        40                              45                            50 | 197 |
| ACA AAA ACA TCT TTG GAA GTT TCT TTG CTA GAA AAA TAT CCG TGC TCC<br>Thr Lys Thr Ser Leu Glu Val Ser Leu Leu Glu Lys Tyr Pro Cys Ser<br>55                                60                            65 | 245 |
| AAG TTT ATA ATT GCT ATA GGA AAT AAT GCA GTA GCA TTT CTG TCA TCA<br>Lys Phe Ile Ile Ala Ile Gly Asn Asn Ala Val Ala Phe Leu Ser Ser<br>70                                75                            80                            85 | 293 |
| TTT GTT ATG AAT TCA GGA GTC TGG GAG GAA GTT GGT TGT GCC AAA CTC<br>Phe Val Met Asn Ser Gly Val Trp Glu Glu Val Gly Cys Ala Lys Leu<br>                  90                              95                            100 | 341 |
| TGG AAT GAA TGG TGT AGA ACA ACA GAC ACT ACA CAT CTG TCC TCC ACA<br>Trp Asn Glu Trp Cys Arg Thr Thr Asp Thr Thr His Leu Ser Ser Thr<br>                        105                              110                            115 | 389 |
| GAG GCT TTT TGT GTG TTT TAT CAT CTA AAA TCC AAT CCC TCG GTT TTT<br>Glu Ala Phe Cys Val Phe Tyr His Leu Lys Ser Asn Pro Ser Val Phe<br>        120                              125                            130 | 437 |
| CTC TGT CAG TGC AGT TGC TAT GTT GCA GAA GAT CAA CAG TAT CAG TGG<br>Leu Cys Gln Cys Ser Cys Tyr Val Ala Glu Asp Gln Gln Tyr Gln Trp<br>        135                              140                            145 | 485 |
| CTG GAA AAG GTT TTT GGC TCT TGT CCA AGG AAG AAC ATG CAG ATA ACT<br>Leu Glu Lys Val Phe Gly Ser Cys Pro Arg Lys Asn Met Gln Ile Thr<br>150                              155                            160                            165 | 533 |
| ATT CTC ACA TGT CGA CAT GTT ACC GAT TAT AAA ACC TCA GAA TCC ACC<br>Ile Leu Thr Cys Arg His Val Thr Asp Tyr Lys Thr Ser Glu Ser Thr<br>                        170                              175                            180 | 581 |
| GGC AGC CTT CCT TCT CCT TTC CTG AGA GCC CTA AAA ACA CAG AAT TTC<br>Gly Ser Leu Pro Ser Pro Phe Leu Arg Ala Leu Lys Thr Gln Asn Phe<br>        185                              190                            195 | 629 |
| AAA GAC TCG GCG TGT TGT CCA TTG CTA GAA CAA CCG AAT ATA GTA CAC<br>Lys Asp Ser Ala Cys Cys Pro Leu Leu Glu Gln Pro Asn Ile Val His<br>                200                              205                            210 | 677 |
| GAC CTT CCT GCA GCA GTT CTA AGC TAC TGT CAA GTA TGG AAA ATC CCA<br>Asp Leu Pro Ala Ala Val Leu Ser Tyr Cys Gln Val Trp Lys Ile Pro<br>215                              220                            225 | 725 |
| GCA ATT CTG TAC TTG TGT TAT ACT GAT GTG ATG AAA TTA GAC CTA ATC<br>Ala Ile Leu Tyr Leu Cys Tyr Thr Asp Val Met Lys Leu Asp Leu Ile<br>230                              235                            240                            245 | 773 |
| ACA GTG GAA GCT TTT AAG CCT ATA CTT TCT ACC AGA AGC TTG AAG GGT<br>Thr Val Glu Ala Phe Lys Pro Ile Leu Ser Thr Arg Ser Leu Lys Gly<br>        250                              255                            260 | 821 |
| TTG GTT AAG AAT ATT CCC CAA AGC ACT GAG ATA CTA AAG AAA TTG ATG<br>Leu Val Lys Asn Ile Pro Gln Ser Thr Glu Ile Leu Lys Lys Leu Met<br>                265                              270                            275 | 869 |
| ACA ACA AAT GAG ATT CAG AGT AAC ATT TAT ACA TGATCTTAAA CATTGTTTTG<br>Thr Thr Asn Glu Ile Gln Ser Asn Ile Tyr Thr<br>        280                              285 | 922 |
| TAGTGTATAT TACTTGTCCA TTCCTTTAAG GGGAGCAGCC TGCACTCTTT TGTAGATTAC | 982 |
| TTTTGGGGGA TATATTTTGA GAATGATGAA ACGGAATAAA ATTGTAAAAA ACTAAAAAAA | 1042 |
| AAAAAAAAAA A | 1053 |

(2) INFORMATION FOR SEQ ID NO:2:

(i) SEQUENCE CHARACTERISTICS:
        (A) LENGTH: 288 amino acids
        (B) TYPE: amino acid (D) TOPOLOGY: linear (ii) MOLECULE TYPE: protein (xi) SEQUENCE DESCRIPTION: SEQ ID NO:2:

```
Met Ala Ala Thr Phe Phe Gly Glu Val Val Lys Ala Pro Cys Arg Ala
 1               5                  10                  15

Gly Thr Glu Asp Glu Glu Glu Glu Gly Arg Arg Glu Thr Pro
            20                  25                  30

Glu Asp Arg Glu Val Arg Leu Gln Leu Ala Arg Lys Arg Glu Val Arg
        35                  40                  45

Leu Leu Arg Arg Gln Thr Lys Thr Ser Leu Glu Val Ser Leu Leu Glu
50                  55                  60

Lys Tyr Pro Cys Ser Lys Phe Ile Ile Ala Ile Gly Asn Asn Ala Val
 65                  70                  75                  80

Ala Phe Leu Ser Ser Phe Val Met Asn Ser Gly Val Trp Glu Val
                85                  90                  95

Gly Cys Ala Lys Leu Trp Asn Glu Trp Cys Arg Thr Thr Asp Thr Thr
                100                 105                 110

His Leu Ser Ser Thr Glu Ala Phe Cys Val Phe Tyr His Leu Lys Ser
                115                 120                 125

Asn Pro Ser Val Phe Leu Cys Gln Cys Ser Cys Tyr Val Ala Glu Asp
130                 135                 140

Gln Gln Tyr Gln Trp Leu Glu Lys Val Phe Gly Ser Cys Pro Arg Lys
145                 150                 155                 160

Asn Met Gln Ile Thr Ile Leu Thr Cys Arg His Val Thr Asp Tyr Lys
                165                 170                 175

Thr Ser Glu Ser Thr Gly Ser Leu Pro Ser Pro Phe Leu Arg Ala Leu
                180                 185                 190

Lys Thr Gln Asn Phe Lys Asp Ser Ala Cys Cys Pro Leu Leu Glu Gln
                195                 200                 205

Pro Asn Ile Val His Asp Leu Pro Ala Ala Val Leu Ser Tyr Cys Gln
210                 215                 220

Val Trp Lys Ile Pro Ala Ile Leu Tyr Leu Cys Tyr Thr Asp Val Met
225                 230                 235                 240

Lys Leu Asp Leu Ile Thr Val Glu Ala Phe Lys Pro Ile Leu Ser Thr
                245                 250                 255

Arg Ser Leu Lys Gly Leu Val Lys Asn Ile Pro Gln Ser Thr Glu Ile
                260                 265                 270

Leu Lys Lys Leu Met Thr Thr Asn Glu Ile Gln Ser Asn Ile Tyr Thr
                275                 280                 285
```

(2) INFORMATION FOR SEQ ID NO:3:

(i) SEQUENCE CHARACTERISTICS:
        (A) LENGTH: 216 base pairs
        (B) TYPE: nucleic acid
        (C) STRANDEDNESS: both
        (D) TOPOLOGY: linear     (ii) MOLECULE TYPE: cDNA     (xi) SEQUENCE DESCRIPTION: SEQ ID NO:3:

```
CCGCGGCGCT GCAGTTGTGT CCAGCCGGTC ACGGGGCGGC TATGGCGGCC ACGTTCTTCG        60

GAGAGGTGGT GAAGGCGCCG TGCCGTGCTG GGACTGAGGA CGAAAGAGGA GGAGGAGGAG       120

GGGGGCGGAG GGAGACGCCG AGGGACAGGG ATGTGCGTCT GCAGCTGCGC GGAAGGGGGG       180

AAGTGCGCAC CAACGAGCAC AAACTCTTGA GTTCTT                                 216
```

(2) INFORMATION FOR SEQ ID NO:4:

(i) SEQUENCE CHARACTERISTICS:
        (A) LENGTH: 20 base pairs
        (B) TYPE: nucleic acid
        (C) STRANDEDNESS: single
        (D) TOPOLOGY: linear     (ii) MOLECULE TYPE: DNA     (xi) SEQUENCE DESCRIPTION: SEQ ID NO:4:

```
CCTGATGCTC GAGTGAATTC                                              20
```

(2) INFORMATION FOR SEQ ID NO:5:

(i) SEQUENCE CHARACTERISTICS:
        (A) LENGTH: 20 base pairs
        (B) TYPE: nucleic acid
        (C) STRANDEDNESS: single
        (D) TOPOLOGY: linear     (ii) MOLECULE TYPE: DNA     (xi) SEQUENCE DESCRIPTION: SEQ ID NO:5:

```
AAGCTTCCAC TGTGATTAGG                                              20
```

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear     (ii) MOLECULE TYPE: DNA (xi) SEQUENCE DESCRIPTION: SEQ ID NO:6:

```
CACAGAATTT CAAAGACTCG G                                            21
```

(2) INFORMATION FOR SEQ ID NO:7:

(i) SEQUENCE CHARACTERISTICS:
        (A) LENGTH: 418 base pairs
        (B) TYPE: nucleic acid
        (C) STRANDEDNESS: both
        (D) TOPOLOGY: both     (ii) MOLECULE TYPE: cDNA     (xi) SEQUENCE DESCRIPTION: SEQ ID NO:7:

```
GGCGGAGCTG AGGGACCATG GCTGCCACGT TCTTTGGCGA GGTGGTGAAG GCGCCGTGCA    60

GAGCTGGGAC TGAGGAGGAA GAAGAGGAGG AGGAGCAGAG CAGGCGGGAC ACGCCGGAGG   120

ACCGGGAGGT CGCGGCAGCT GGCGCGGAAG AGGGAGGTTC GGCTTCTCCG AAGACAGACA   180

GAAACATCTC TGGAGGCTGT GCTCCTAGAG ACACACCCTT GCTCCAAGTT TATAATTGCA   240

GTAGGAAGCA ACGAACAGC ATTCCTGTCA GCGTTTGTTA TGAACTCGGG AGTCTGGGAA    300

GAAGTCGGTT GTGCTAAGCT CTGGAATGAA TGGTGCAGAA CTACAGACAC TGTCCGTACT   360

GTTCCCCTAC AGATGTTTCT GTGTGTTTAT CAACTGAATC AGATCCTCGG TTTCTATG     418
```

(2) INFORMATION FOR SEQ ID NO:8:

(i) SEQUENCE CHARACTERISTICS:
        (A) LENGTH: 420 base pairs
        (B) TYPE: nucleic acid
        (C) STRANDEDNESS: both (D) TOPOLOGY: both (ii) MOLECULE TYPE: cDNA (xi) SEQUENCE DESCRIPTION: SEQ ID NO:8:

| | | | | | | |
|---|---|---|---|---|---|---|
| TGCAGCTTCT | CTCCTTCCTG | AGAGCCTAAA | CTCAGACATT | CAAGATGCCC | TCTGCTGCCC | 60 |
| ACTGGCTGGA | ACAGCCGAAC | ATTGTGCATG | ACCTGTCTGC | AGCAGTTCTG | AGCTACTGTC | 120 |
| AAGTATGGAA | AACCCTGCGG | TTCTGTATCT | GTGCTACACT | GATGTGATGA | AGGTGGCACT | 180 |
| CGTGTCACGG | TTGAAGCTTT | TAAACCGTTA | CTCTCCTCCA | GGAGCTTGAA | ATGCTTGGTG | 240 |
| AAGAACATTC | CTGAAAGCAC | AGAAACTCTG | AAGAAGTTGA | TGACCACAAA | TGAGATTCAG | 300 |
| AGCAACATTT | ACACATGACC | CCAGGTGGCC | AGGACCTGCC | TGCTCCAGGG | GGCAGTCACT | 360 |
| GATGTTTTGT | ATTTTATTCT | GGCTTGGGAT | GTTTTGAGAG | TAATAAAAAT | TTTAAAAATT | 420 |